US010285577B2

(12) United States Patent
Czupalla et al.

(10) Patent No.: US 10,285,577 B2
(45) Date of Patent: May 14, 2019

(54) COOLING OF A MEDICAL INSTRUMENT

(71) Applicant: Karl Storz SE & Co. KG, Tuttlingen (DE)

(72) Inventors: Christian Czupalla, Singen (DE); Markus Kupferschmid, Emmingen-Liptingen (DE); Andreas Heni, Fridingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 1010 days.

(21) Appl. No.: 14/495,296

(22) Filed: Sep. 24, 2014

(65) Prior Publication Data
US 2015/0087998 A1 Mar. 26, 2015

(30) Foreign Application Priority Data

Sep. 24, 2013 (DE) ........................ 10 2013 110 587

(51) Int. Cl.
| A61B 1/12 | (2006.01) |
|---|---|
| A61B 5/00 | (2006.01) |
| A61B 1/00 | (2006.01) |
| G02B 23/24 | (2006.01) |
| A61B 1/002 | (2006.01) |
| A61B 1/06 | (2006.01) |
| A61B 90/30 | (2016.01) |
| A61B 90/00 | (2016.01) |

(52) U.S. Cl.
CPC ............. *A61B 1/128* (2013.01); *A61B 1/002* (2013.01); *A61B 1/00006* (2013.01); *A61B 5/0077* (2013.01); *G02B 23/2476* (2013.01); *A61B 1/0669* (2013.01); *A61B 2090/306* (2016.02); *A61B 2090/309* (2016.02); *A61B 2090/3616* (2016.02)

(58) Field of Classification Search
None
See application file for complete search history.

(56) References Cited

U.S. PATENT DOCUMENTS

| 3,299,884 | A | 1/1967 | Moore et al. | |
|---|---|---|---|---|
| 2003/0214579 | A1 | 11/2003 | Iddan | |
| 2005/0158687 | A1 | 7/2005 | Dahm | |
| 2006/0004276 | A1 | 1/2006 | Iddan et al. | |
| 2007/0191684 | A1* | 8/2007 | Hirata | A61B 1/00096 600/179 |
| 2012/0120635 | A1* | 5/2012 | Strong | F21V 21/084 362/105 |
| 2015/0282695 | A1* | 10/2015 | Tay | A61B 1/00135 600/124 |

FOREIGN PATENT DOCUMENTS

WO 2011058505 A1 5/2011

* cited by examiner

*Primary Examiner* — Bo Joseph Peng
(74) *Attorney, Agent, or Firm* — Whitmyer IP Group LLC

(57) ABSTRACT

A medical instrument includes a hermetically tight sheath, a heat source, a surface area thermally coupled to the heat source, a rotor arranged outside the hermetically tight sheath and serving to generate a flow of fluid at the surface, a magnet at the rotor, and means for generating a variable magnetic field in order to move the rotor. The means for generating a variable magnetic field is arranged inside the hermetically tight sheath.

21 Claims, 4 Drawing Sheets

COOLING OF A MEDICAL INSTRUMENT

FIELD OF THE INVENTION

The present invention relates to an exoscope, an endoscope or another medical instrument, and in particular to the cooling of the medical instrument.

BACKGROUND OF THE INVENTION

Exoscopes, endoscopes and other medical instruments can contain image sensors, processors and other circuitry for processing image data and other data, power electronics, light-emitting diodes or other light sources and other heat sources. Normally, the thermal output generated by these heat sources is carried off mainly by natural convection, which is driven by the heating of the air surrounding the medical instrument. The continuing process of miniaturization of electronic components, their increasing performance and their availability at ever lower costs cause that medical instruments contain an increasing number of electronic components with increasing thermal output. Heat dissipation by means of natural convection is therefore no longer sufficient in all cases. A conventional fan or compressor, for forcing convection or a cooling flow of fluid, cannot readily be cleaned and autoclaved and is therefore not considered for use with many medical instruments.

SUMMARY OF THE INVENTION

It is an object of the present invention to make available an improved medical instrument which in particular is better cooled and at the same time can be easily cleaned and preferably autoclaved.

This object is achieved by the subjects of the independent claims.

Developments are set forth in the dependent claims.

A medical instrument comprises a liquid-tight sheath, a heat source, a surface area thermally coupled to the heat source, a rotor arranged outside the hermetically tight sheath and serving to generate a flow of fluid at the surface, a magnet at the rotor, and means for generating a variable magnetic field in order to move the rotor.

A medical instrument comprises a fluid-tight or at least liquid-tight sheath, a heat source, a surface area thermally coupled to the heat source, a rotor arranged outside the sheath and serving to generate a flow of fluid at the surface, a magnet at the rotor, and means for generating a variable magnetic field in order to move the rotor, the means being arranged inside the fluid-tight sheath.

In particular, the medical instrument is an exoscope or an endoscope.

An exoscope is a device provided and designed for extracorporeal use, for visual inspection or observation of objects in medicine, in particular of objects at or near outer surfaces of a human or animal body. In contrast to an endoscope, an exoscope is not designed to be inserted through a small natural or artificial opening into a natural or artificial cavity. Instead, an exoscope is designed for observation of an object which is visible from outside, at least during observation, in particular during an operation. Accordingly, during its intended use, the exoscope is located entirely outside the human or animal body and, in contrast to the endoscope, does not necessarily have a long thin shaft.

An exoscope can have one or more cameras or light-sensitive image sensors for two-dimensional or three-dimensional capturing and displaying, for example on a screen. Alternatively, an exoscope is monocular or binocular for direct observation with the human eye. An exoscope is generally designed or optimized for an object distance in the range of a few centimeters or a few decimeters. An exoscope can have a high magnification, facilitating a resolution not attainable with the naked eye, and it can thus have properties of a magnifier or stereo magnifier or of a microscope or stereo microscope. The exoscope generally differs from the microscope or stereo microscope in having a greater object distance.

The sheath is in particular hermetically tight. The hermetically tight sheath in particular encloses the observation beam path. Moreover, the hermetically tight sheath can enclose the illumination beam path and/or other parts of the medical instrument. All the components and structural parts of the medical instrument arranged inside the hermetically tight sheath are protected there, in particular from water vapor and other damaging fluids. All the components and structural parts of the medical instrument arranged inside the hermetically tight sheath cannot become soiled and therefore also do not have to be cleaned. In particular, the outer surface of the hermetically tight sheath is as far as possible substantially smooth and convex, in order to make cleaning easier.

The heat source comprises in particular an image sensor, a processor or another circuit for preparing or processing image data and/or other data, a light-emitting diode or another lighting means and/or power electronics for supplying electrical power to a lighting means, a processor or a circuit. The heat source is in particular arranged in a handle or grip at the proximal end of the medical instrument and/or at the distal end of the medical instrument. The heat source is in particular arranged inside the hermetically tight sheath. The exoscope can comprise a plurality of the heat sources described.

The surface area thermally coupled to the heat source is in particular an area of the outer surface of the hermetically tight sheath. The surface area is coupled to the one or more heat sources of the medical instrument in particular by heat conduction, radiation and/or convection inside the hermetically tight sheath.

The rotor is in particular designed to generate a flow of ambient air or a flow of carbon dioxide, water or another surrounding medium of the medical instrument. The rotor can generate a flow of fluid at the surface thermally coupled to the heat source, by conveying ambient air toward the surface area and/or by conveying ambient air away from the surface area. The rotor comprises in particular a plurality of permanent magnets with alternately oriented polarity.

The means for generating a variable magnetic field is in particular designed to generate a rotating or substantially rotating magnetic field. The means comprises in particular a plurality of rigidly arranged electromagnets or coils. The means for generating a variable magnetic field and the rotor act in particular like the stator and rotor of a synchronous or asynchronous polyphase motor.

Means for powering the electromagnets and in particular for generating currents with different phases in the electromagnets can in particular be provided inside the hermetically tight sheath. Alternatively, alternating currents for the electromagnets can be provided by a separate device and can be transmitted to the medical instrument by means of electrical lines.

Alternatively, the means for generating a variable magnetic field comprises one or more permanent magnets which are rotatable about an axis and are coupled to an electric motor, an ultrasonic motor or another drive.

The rotor can be provided with a smooth surface which can be easily cleaned, or it can be designed as a disposable product that is discarded after one use and is replaced by a new and sterile rotor. The means for generating a variable magnetic field is protected inside the hermetically tight sheath from soiling and from the effect of water vapor and other damaging fluids. Thus, by arranging only the rotor outside the sheath, and arranging the means for generating a variable magnetic field inside the hermetically tight sheath, it is possible to simplify, or indeed actually permit, the cleaning of the medical instrument.

By means of a flow of fluid being generated at the surface area thermally coupled to the heat source, the rotor facilitates effective removal of the thermal output generated by the heat source. Therefore, the medical instrument can have, for example, a greater number of circuits, and more complex circuits, for preparing and processing image data, a stronger light source or a brighter lighting means and/or other functions that generate waste heat.

In a medical instrument as described herein, the means for generating a variable magnetic field is provided and designed in particular to generate a rotating magnetic field.

The means for generating a variable magnetic field comprises in particular at least three electromagnets, which are provided such that alternating currents with a mutual phase difference of 120 degrees flow in them.

In a medical instrument as described herein, the means for generating a variable magnetic field is in particular also designed for magnetically bearing the rotor.

By virtue of a magnetic and therefore contactless bearing of the rotor, deterioration and wear can be avoided, friction can be reduced or entirely avoided, and therefore the required drive power can be reduced and low-noise operation can be facilitated. An additional emergency bearing can be provided in order to avoid, in the event of an unforeseen external action or a failure of the means for generating a variable magnetic field, a collision between the rotor and other parts of the medical instrument, abrasion, damage or destruction of the rotor, and contamination of a patient with abrasion particles. The emergency bearing comprises, for example, a structural part in the shape of a bearing shell made of polytetrafluoroethylene (PTFE; also known under the brand name Teflon) or another tough material that facilitates low friction.

In a medical instrument as described herein, the rotor is provided and designed in particular to generate a flow of fluid in a direction from proximal to distal.

A medical instrument as described herein is designed in particular to generate a flow of fluid at the distal end of the medical instrument.

For this purpose, the rotor and optionally one or more means for guiding a flow of fluid generated by the rotor can be arranged at or near the proximal end of the medical instrument and designed in order to generate a flow of fluid from proximal to distal.

In a medical instrument as described herein, the rotor is arranged in particular at or near the distal end of the medical instrument.

In a medical instrument as described herein, the rotor is in particular designed to generate a flow of fluid in a direction from distal to proximal. For this purpose, the rotor is in particular arranged at or near the distal end of the medical instrument.

In a medical instrument as described herein, the rotor is in particular movable in a direction parallel to a longitudinal axis of the medical instrument.

The mobility of the rotor in a direction parallel to the longitudinal axis of the medical instrument can simplify, or indeed actually permit, complete cleaning and sterilization of the medical instrument. The rotor is movable in particular between two or more positions, in each of which it is held and can be driven magnetically. The rotor can be movable between these positions manually, magnetically or by some other drive means.

In a medical instrument as described herein, the rotor can in particular be separated from other parts of the medical instrument in a non-destructive and reversible manner.

The rotor can in particular be separated from other parts or the rest of the medical instrument by being moved in the distal direction and past the distal end of the medical instrument. Alternatively, the rotor can be separated by a movement in the proximal direction and past the proximal end of the medical instrument. The removability of the rotor can simplify the cleaning of the medical instrument and allow the rotor to be exchanged in the event of damage or destruction.

In a medical instrument as described herein, at least one of the means for generating a variable magnetic field is movable between several positions and several devices for generating a variable magnetic field are provided, so as to be able to drive the rotor at several positions.

The in particular manual or magnetic mobility of the rotor, between at least two positions where the rotor can be rotated, can facilitate different cooling modes. In particular, the rotor can be arranged alternately at or near the proximal end of the medical instrument or at or near the distal end of the medical instrument, in order to particularly cool different areas of the medical instrument. By providing means for generating a variable magnetic field at each position where the rotor is intended to be held and rotated, a rigid and therefore particularly robust configuration of these means for generating variable magnetic fields can be facilitated. In particular, a mobility of means for generating a variable magnetic field can facilitate a positioning and driving or operation of the rotor at any desired or almost any desired location along the path on which the means for generating a variable magnetic field is movable.

A medical instrument as described herein further comprises in particular a controller for controlling the means for generating a variable magnetic field, wherein the controller is designed to control at least one of the rotational direction and the rotational speed of the rotor.

A controller for controlling the means for generating a variable magnetic field can, in particular by controlling the rotational speed, facilitate an adjustment or variation of the cooling power and/or, by controlling or switching the rotational direction, can facilitate a movement of the area of maximum cooling at the medical instrument.

A medical instrument as described herein further comprises in particular means for detecting a temperature of the heat source, wherein the controller is coupled to the means for detecting the temperature and is designed to control at least one of the rotational direction and the rotational speed of the rotor depending on the temperature of the heat source.

The means for detecting a temperature of the heat source comprises in particular a sensor for direct or indirect detection of the temperature of the heat source, which sensor is arranged at or in the heat source. Alternatively, the means for detecting the temperature of the heat source comprises a signal input for receiving a sensor signal from a sensor for direct or indirect detection of the temperature of the heat source. The temperature of the heat source can, for example, be detected by measuring the voltage at a thermocouple, the voltage at, the current in or the resistance of an element with temperature-dependent resistance, a current consumption of the heat source, a supply voltage at the heat source and/or one or more other parameters.

A medical instrument as described herein further comprises in particular two means for detecting respectively the temperature of one of two heat sources, wherein the controller is connected to the two devices for detecting the temperatures of the heat sources and is designed to control the rotational direction of the rotor depending on the temperatures of the heat sources.

In particular, the medical instrument comprises a first heat source (for example a light source or image sensor) at the distal end and a second heat source (for example a processor or another circuit for processing or preparing image data) at the proximal end. The controller is designed to control a first rotational direction of the rotor and a flow of fluid in the distal direction when the first heat source requires more cooling than the second heat source, and to control a second rotational direction of the rotor and a flow of fluid in the proximal direction when the second heat source requires more cooling.

A medical instrument as described herein is in particular an endoscope, an exoscope or a surgical microscope.

A medical instrument as described herein also comprises in particular a guiding means for guiding or diverting a flow of fluid generated by the rotor.

The guiding means comprises in particular a jacket for keeping the flow of fluid at the surface portion thermally coupled to the heat source or for guiding the flow of air to the surface portion thermally coupled to the heat source.

Alternatively or in addition, the guiding means can comprise one or more guide grates and/or one or more guide blades for guiding the flow of fluid in a desired direction and/or for shaping a flow of fluid to a desired cross section or a desired speed profile.

In a medical instrument as described herein, in particular at least one of the rotor and the guiding means is designed to generate a flow of fluid which extends, at least in part, helically around a shaft of the medical instrument.

For this purpose, the guiding means in particular comprises helically curved or helically wound guide blades and/or a jacket by which a flow of fluid already generated helically by the rotor is guided to the shaft. A flow of fluid extending helically around the shaft can be laminar to a particularly long portion of the shaft and can thus, for example, extend the cooling action of the flow of fluid particularly far in the distal direction from the rotor arranged at the proximal end.

A medical instrument as described herein further comprises in particular means for converting a laminar flow to a turbulent flow.

The means for converting a laminar flow to a turbulent flow comprises in particular one or more turbulators, or turbulence or vortex generators, as are known in particular from aeronautics. The means for converting a laminar flow to a turbulent flow is in particular arranged upstream from the surface portion thermally coupled to the heat source. By means of laminar flow up to or almost up to the surface portion thermally coupled to the heat source, it is possible for the flow of fluid, with comparatively small losses, to reach as far as the surface portion thermally coupled to the heat source. By means of a turbulent flow at the surface portion thermally coupled to the heat source, the heat transfer between the surface and the flow of fluid can be improved, and therefore also the cooling performance.

BRIEF DESCRIPTION OF THE DRAWINGS

Embodiments are explained in more detail below with reference to the attached figures, where.

DETAILED DESCRIPTION OF THE INVENTION

Figure 1:
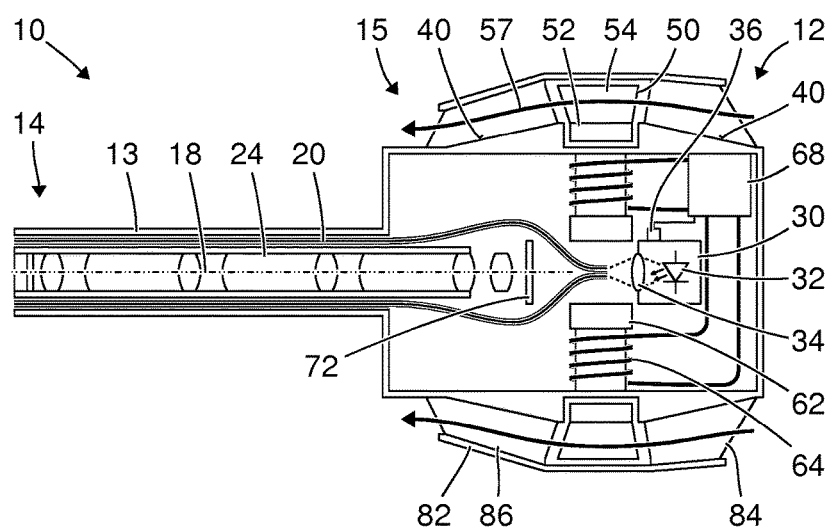
FIG. 1 shows a schematic view of an exoscope.

FIG. 1 shows a schematic view of an exoscope 10 with a proximal end 12 and a distal end 14. The exoscope 10 comprises a shaft 13, which in particular has a circular cylindrical or substantially circular cylindrical outer shape with an axis of symmetry 18. This axis of symmetry 18 is also referred to hereinbelow as the longitudinal axis of the exoscope 10. The exoscope 10 further comprises a handle 15 at the proximal end 12.

The view of the exoscope 10 in FIG. 1 is similar to a cross-sectional view. In contrast to a true cross-sectional view, a number of components and structural parts of the exoscope 10 are each indicated in plan view and section surfaces are not hatched.

The exoscope 10 comprises a hermetically tight sheath 20, which in particular is composed of a plurality of parts cohesively or coalescently joined to one another. Arranged inside the hermetically tight sheath 20 are optical fibers 22, by means of which illumination light generated by a light source 30 at the proximal end 12 of the exoscope 10 is transmitted to the distal end 14. Moreover, a beam path 24 for observation light is provided inside the hermetically tight sheath 20 and in particular in the area of the shaft 13. The beam path 24 is provided such that light emanating from an object to be viewed is transmitted to an image sensor 72 arranged in the handle 15. The light source 30 comprises in particular one or more light-emitting diodes 32 and a lens 34 or other devices which ensure that as much as possible of the light generated by the light-emitting diode 32 is coupled into the optical fibers 22.

The light source 30, the optical fibers 22, the image sensor 72 and devices (not shown in FIG. 1) for preparing and processing an image signal generated by the image sensor 72 and/or for controlling the light source 30 are examples of heat sources inside the hermetically tight sheath 20. Since no substance exchange takes place between the inside of the hermetically tight sheath 20 and the environment of the exoscope 10, all of the heat generated by the heat sources has to be released to the environment of the exoscope 10 via the hermetically tight sheath 20.

In the area of the handle 15 of the exoscope 10, an axial compressor or a rotor 50 is arranged which, in particular, is rotatable about the longitudinal axis 18 of the exoscope 10. The rotor 50 comprises a ring 52, at the outer circumference of which blades 54 are arranged substantially in a radial direction. Proximal guide blades 84 are arranged proximally from the rotor 50, in particular proximally from the blades 54 of the rotor 50. Distal guide blades 86 are arranged distally from the rotor 50. An annular jacket 82 connects the radially outer ends of the proximal and distal guide blades 84, 86 and encloses the rotor 50. The blades 54 of the rotor 50 are designed in such a way that a rotation of the rotor 50 in a predetermined rotational direction about the longitudinal axis 18 of the exoscope 10 generates a proximal to distal air flow 57 in the annular space between the hermetically tight sheath 20 and the jacket 82. The air flow 57 generated by the rotating rotor 50 is substantially parallel to the longitudinal axis 18 of the exoscope 10.

A magnetic flux conductor 62, several conductor coils 64 at the magnetic flux conductor 62, and a controller 68 coupled to the conductor coils 64 are arranged inside the hermetically tight sheath 20. The controller 68 comprises several power sources for generating alternating currents in the conductor coils 64. The magnetic flux conductor 62, the conductor coils 64 and the controller 68 form means for generating a variable magnetic field. The controller 68 is designed to generate alternating currents of identical frequency and of differing phase position in the magnetic flux conductors 62, such that the conductor coils 64 generate corresponding magnetic alternating fields. The controller 68 is in particular designed to generate, by means of the conductor coils 64, a substantially rotating magnetic field for moving or driving the rotor 50. To ensure that the rotor 50 can be driven by the rotating magnetic field generated by the controller 68 via the conductor coils 64, the ring 52 and/or the blades 54 of the rotor 50 are magnetizable or magnetized. Alternatively or in addition, the rotor 50 can be designed to be electrically conductive, in order to facilitate an induction of eddy currents in the rotor 50 by a rotating magnetic field.

The controller 68 is coupled to one or more temperature sensors 36 at the light source 30 and/or at one or more other heat sources inside the hermetically tight sheath 20. Alternatively or in addition, the controller 68 can have one or more signal inputs for detecting currents, voltages, resistances or other parameters, from which it is possible to calculate or estimate the temperature or the temperatures of one or more heat sources. The controller 68 is designed to control currents in the conductor coils 64 in accordance with the one or more temperatures. In particular, the controller 68 is designed to drive the rotor 50 only when a predetermined temperature threshold is exceeded, or to drive the rotor 50 more quickly when a detected temperature has a higher value and more slowly when the detected temperature has a lower value. Moreover, the controller 68 can be designed to reverse the rotational direction of the rotor 50, particularly in accordance with several detected temperatures.

The controller 68 can furthermore be designed to control currents in the conductor coils 64 in such a way that the rotor 50 does not touch the hermetically tight sheath 20, the jacket 82 or any other parts of the exoscope 10 but instead rotates with magnetic support in a manner free of contact and therefore free of wear.

The light source 30 and, if appropriate, further heat sources inside the hermetically tight sheath 20 are coupled to said hermetically tight sheath 20, in particular to an outer surface area 40 of the hermetically tight sheath 20, by heat radiation, heat conduction in a medium filling the inside of the hermetically tight sheath 20, by convection in this medium and/or by a heat conductor not shown in FIG. 1. The heat generated by the heat source 30, 72 is carried off, by an airflow 57 generated by the rotating rotor 50, along the surface 40 coupled to the heat source 30, 72.

Figure 2:
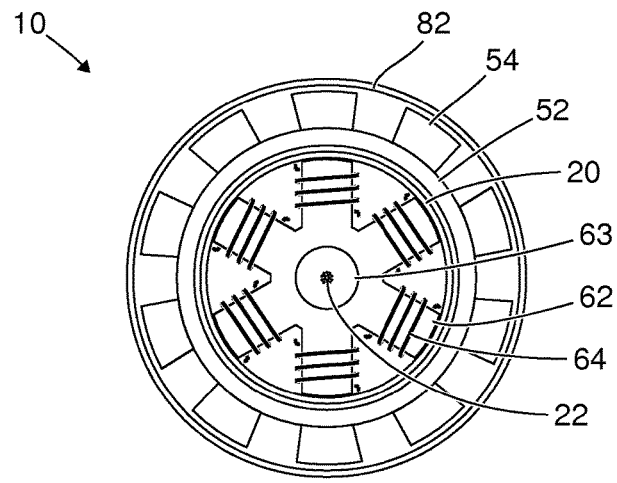
FIG. 2 shows a further schematic view of the exoscope from FIG. 1.

FIG. 2 shows a further schematic view of the exoscope 10 from FIG. 1. The plane of the drawing of FIG. 2 is orthogonal to the plane of the drawing of FIG. 1 and orthogonal to the longitudinal axis 18 of the exoscope 10. FIG. 2 shows the exoscope 10 cut open along a surface orthogonal to the longitudinal axis 18 and close to the magnetic flux conductor 62, the conductor coils 64 and the rotor 50. Just as in FIG. 1, section surfaces are not hatched in FIG. 2, in contrast to many cross-sectional views.

The magnetic flux conductor 62 has approximately the shape of a star whose radial portions are each surrounded by a conductor coil 64. Moreover, the magnetic flux conductor 62 has a central through-opening 63 in which the optical fibers 22 are arranged. The radially outer end faces of the radial portions of the magnetic flux conductor 62 abut on the inner surface of the hermetically tight sheath 20. The ring 52 and the blades 54 of the rotor 50 are arranged concentrically with respect to the circular cylindrical hermetically tight sheath 20 and radially spaced apart therefrom in the area shown. The rotor 50 is surrounded by the annular jacket 82. The jacket 82 is spaced apart from the radially outer ends of the blades 54 of the rotor 50.

Figure 3:
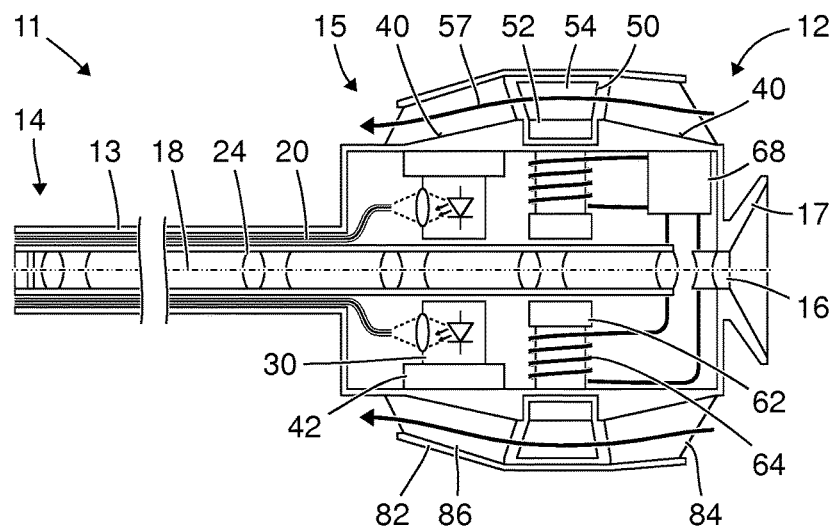
FIG. 3 shows a schematic view of an endoscope.

FIG. 3 shows a schematic view of an endoscope 11. The manner in which the endoscope 11 is shown in FIG. 3 corresponds to the manner in which the exoscope is shown in FIG. 1.

The endoscope 11 is similar, in some features and properties, to the exoscope 10 shown in FIGS. 1 and 2. Features and properties of the endoscope 11 are set out below which distinguish the latter from the exoscope shown in FIGS. 1 and 2.

The endoscope 11 shown in FIG. 3 has a long shaft 13, which is represented in a shortened form in FIG. 3. The shaft 13 accommodates optical fibers 22 which transmit illumination light and which are coupled to a plurality of light sources 30 inside the handle 15 at the proximal end 12 of the endoscope 11. Each individual light source 30 is in particular similar to the light source shown in FIG. 1. The shaft 13 moreover accommodates a beam path 24 for observation light, which emanates from an object to be observed. The beam path 24 comprises in particular a series of rod lenses indicated in FIG. 3. The beam path 24 extends as far as an eyepiece 16 at the proximal end of the endoscope 11. In order to screen off surrounding light, and optionally to couple a camera to the endoscope 11, an eyepiece cup 17 is provided at the eyepiece 16.

The light sources 30 are coupled to the hermetically tight sheath 20 and in particular to the surface area 40 by means of a heat conductor 42 made of copper, aluminum or another material with high thermal conductivity. The heat conductor 42 is in particular ring-shaped or substantially ring-shaped such that the heat generated by the light sources 30 is carried off via an annular surface area 40 and such that particularly efficient use is made of the annular air flow 57 generated by the rotor 50.

The rotor 50, the jacket 82, the proximal and distal guide blades 84, 86, the magnetic flux conductor 62, the conductor coils 64 and the controller 68 correspond to or are substantially similar to those shown in FIGS. 1 and 2.

In contrast to the view in FIG. 3, one or more temperature sensors at the light sources 30 and/or at other heat sources inside the hermetically tight sheath 20 can be coupled to the controller 68, similarly to the exoscope shown in FIGS. 1 and 2.

Figure 4:
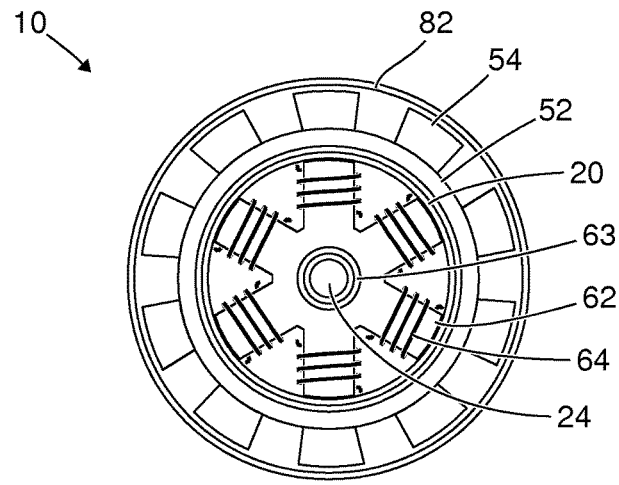
FIG. 4 shows a further schematic view of the endoscope from FIG. 3.

FIG. 4 shows a further schematic view of the endoscope 11 from FIG. 3. The nature of the view in FIG. 4 corresponds to the nature of the view in FIG. 2. In particular, the plane of the drawing of FIG. 4 is orthogonal to the longitudinal axis 18 of the endoscope 11 and to the plane of the drawing of FIG. 3, wherein a cross section is shown along a surface near the rotor 50, the magnetic flux conductor 62 and the conductor coils 64. The beam path 24 for observation light is arranged in the central through-opening 63 of the magnetic flux conductor 62.

Figure 5:
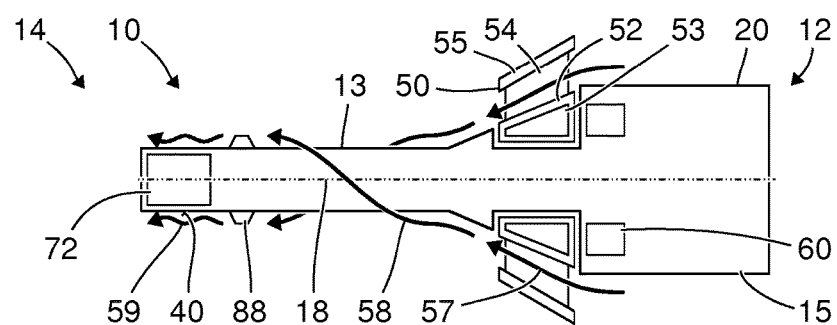
FIG. 5 shows a schematic view of a further exoscope.

FIG. 5 shows a schematic view of a further exoscope 10 which, in some features and properties, is similar to the exoscope shown in FIGS. 1 and 2. As in FIGS. 1 to 4, a cross section through the exoscope is indicated, wherein section surfaces are not hatched. The plane of the drawing or sectional plane of FIG. 5 corresponds to the planes of the drawings or sectional planes of FIGS. 1 and 3. Features and properties of the exoscope 10 are set out below which differ from those of the exoscope shown in FIGS. 1 and 2.

The exoscope 10 has a proximal end 12, a distal end 14, a shaft 13, which extends to the distal end 14, and a handle 15 near the proximal end 12. The exoscope 10 comprises a hermetically tight sheath 20, inside which an image sensor 72 or a camera is arranged near the distal end 14 of the exoscope 10. The image sensor 72 constitutes a heat source, of which the heat has to be carried away. Moreover, the exoscope can have further heat sources not shown in FIG. 5, for example inside the handle 15. These heat sources not shown in FIG. 5 can include devices for preparing or processing an image signal from the image sensor 72 and power electronics for providing electrical power for these devices, for the image sensor 72, for a light source or for other consumers.

Moreover, means 60 for generating a variable magnetic field is arranged inside the hermetically tight sheath 20 and in particular occupies a substantially annular installation space symmetrical to the longitudinal axis 18 of the exoscope 10. Near the means 60 for generating a variable magnetic field, a rotor 50 is arranged outside the hermetically tight sheath, which rotor 50 can rotate about the longitudinal axis 18 of the exoscope 10. The rotor 50 has a ring 52 with magnets 53 embedded therein, blades 54 protruding radially outward from the ring 52, and an annular jacket 55 which connects the radially outer ends of the blades 54 to one another in a ring shape and mechanically supports them. By means of a variable and in particular rotating magnetic field, generated by the means 60, interacting with the magnets 53 in the ring 52 of the rotor 50, the rotor is driven like a rotor of a synchronous three-phase motor and rotates about the longitudinal axis 18 of the exoscope 10. Moreover, the means 60 for generating a variable magnetic field can be designed to support the rotor magnetically or hold it free of contact in a predetermined position.

The rotor 50 and in particular its blades 54 are designed to generate an airflow 57 during rotation about the longitudinal axis 18 of the exoscope 10. The air flow 57 generated by the rotor 50 continues along the shaft 13 in the form of a laminar air flow 58 that helically encloses the shaft 13. Proximally from the surface 40 thermally coupled to the heat source 72, turbulators 88 are arranged at the outer surface of the hermetically tight sheath 20 and cause a transfer from a laminar stream in the air flow 58 to a turbulent stream in the air flow 59 at the surface 40. The turbulent air flow 59 at the surface 40 improves the heat transfer from the surface 40 to the air flow 59 and thereby improves the cooling action.

The rotor 50 rotating in a predetermined rotational direction sucks in ambient air near the outer surface of the hermetically tight sheath 20 in the area of the handle 15. In this way, also in the area of the handle, the rotating rotor 50 generates an air flow that carries off heat from heat sources (not shown in FIG. 5) arranged inside the handle 15.

Figure 6:
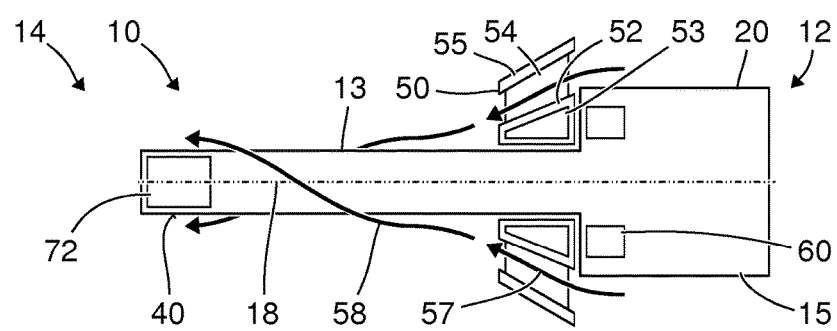
FIG. 6 shows a schematic view of a further exoscope.

FIG. 6 shows a schematic view of a further exoscope 10 which, in some features and properties, is similar to the exoscopes shown in FIGS. 1 and 5, in particular to the exoscope shown in FIG. 5. The nature of the view corresponds to that of FIG. 5. Features and properties of the exoscope 10 are described below which distinguish the latter from the exoscope shown in FIG. 5.

The exoscope shown in FIG. 6 differs from the exoscope shown in FIG. 5 particularly in that no turbulators 88 are provided. Moreover, the hermetically tight sheath 20, particularly in the area of the rotor 50 and of the shaft 13, is designed such that the rotor 50 can be moved in the distal direction starting from the position shown in FIG. 6. The means 60 for generating a variable magnetic field is designed to magnetically support the rotor 50, i.e. to hold the rotor 50 at the intended position shown in FIG. 6, even during rotation, similarly to what is described above with reference to FIGS. 1 and 5.

Figure 7:
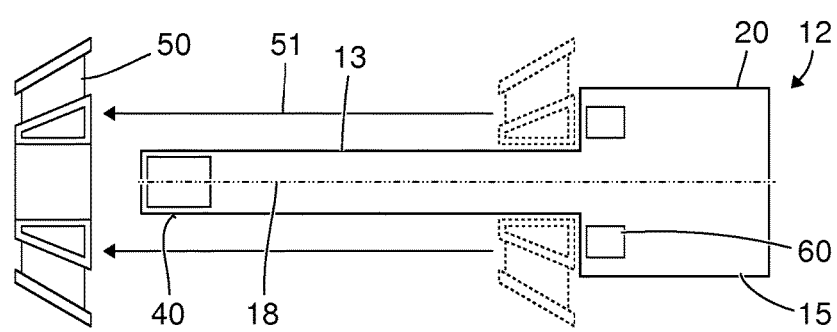
FIG. 7 shows a further schematic view of the exoscope from FIG. 6.

FIG. 7 shows a further schematic view of the exoscope from FIG. 6. The nature of the view in FIG. 7, in particular the plane of the drawing, corresponds to those of FIG. 6. FIG. 7 shows the exoscope 10 in a further configuration. In relation to the position intended for the use of the exoscope 10, which position is shown in FIG. 6 and is also indicated by broken lines in FIG. 7, the rotor 50 has been moved in a direction 51 parallel to the longitudinal axis 18 of the exoscope 10 and beyond the distal end 14 of the exoscope 10. The rotor 50 is thus geometrically and mechanically separated from the rest of the exoscope 10 and can be cleaned and autoclaved independently and, in the event of damage, can be easily replaced.

Figure 8:
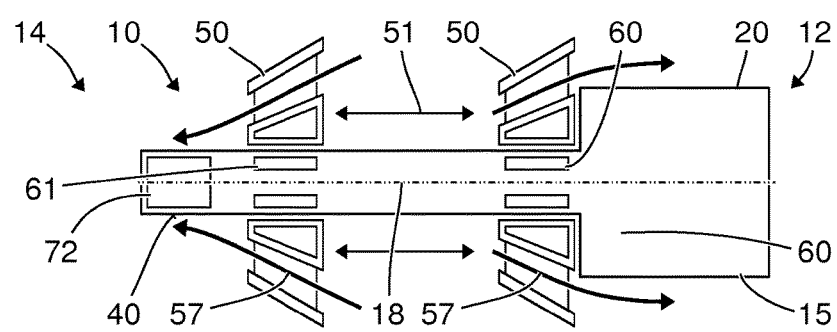
FIG. 8 shows a schematic view of a further exoscope.

FIG. 8 shows a schematic view of a further exoscope 10 which, in some features and properties, is similar to the exoscopes shown in FIGS. 1, 2 and 5 to 7, in particular to the exoscope shown in FIGS. 6 and 7. The nature of the view in FIG. 8 and, in particular, the section surface shown correspond to those of FIGS. 1, 3 and 5 to 7. Features and properties of the exoscope 10 are described below which distinguish the latter from the exoscope shown in FIGS. 6 and 7.

The exoscope shown in FIG. 8 comprises a first means 60 for generating a variable magnetic field near the handle 15 and a second means 61 for generating a variable magnetic field near the distal end 14 of the exoscope 10. Like the devices shown in FIGS. 1 to 7 for generating variable magnetic fields, each of the two devices 60, 61 is similarly provided and designed to generate a substantially rotating magnetic field and by this means to drive the rotor and set it in rotation. Moreover, both devices 60, 61 for generating variable magnetic fields are in particular provided and designed to support the rotor 50 and to hold it in a predetermined position during the rotation. The rotor 50 can thus be operated alternatively in two different positions at the exoscope 10. In FIG. 8, the rotor 50 is shown in each of the two positions.

When the rotor 50 is operated in the distal position, shown on the left-hand side in FIG. 8, the heat source 72 at the distal end 14 of the exoscope 10 is cooled particularly intensively. When the rotor 50 is operated in the proximal position, shown on the right-hand side in FIG. 8, and when the rotational direction is reversed in order to generate an air flow 57 in the opposite direction, the handle 15 is cooled particularly intensively. The exoscope 10 can comprise a controller (not shown in FIG. 8) which, by measuring several temperatures, in particular by measuring the temperatures of several heat sources inside the hermetically tight sheath 20, makes it possible to determine which heat source is most in need of cooling. Depending on the measured temperatures, the controller can then operate the rotor in different positions and/or with different running directions, in order in particular to cool the heat source that has the greatest need of cooling. A movement of the rotor 50 in direction 51 parallel to the longitudinal axis 18 of the exoscope 10, between the two positions shown in FIG. 8 and/or further positions, can take place magnetically or manually, after a prompt generated by the controller 68, at a user interface or some other way.

In a departure from the view shown in FIG. 8, three or more devices for generating variable magnetic fields can be provided. Alternatively, one means for generating a variable magnetic field can be movable inside the hermetically tight sheath 20 (in particular by means of an ultrasonic motor or an electrical drive) in order to operate the rotor 50 at two or more different positions.

Figure 9:
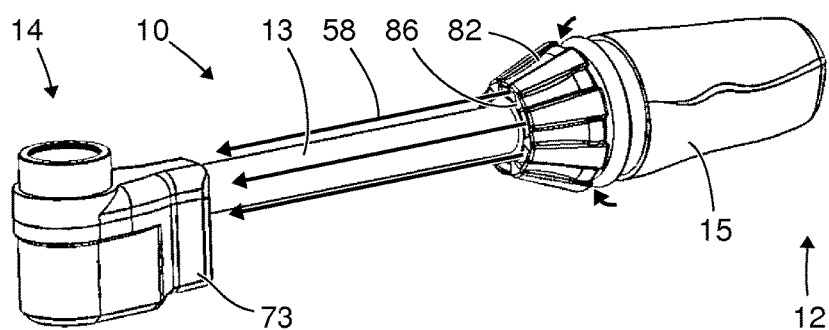
FIG. 9 shows a schematic axonometric view of a further exoscope.

FIG. 9 shows a schematic axonometric view of a further exoscope 10 which, in some features and properties, is similar to the exoscopes shown above in FIGS. 1, 2 and 5 to 8. In particular, the exoscope has heat sources that require cooling.

The exoscope 10 has a handle 15 at the proximal end 12 and a camera housing 73 at the distal end 14. The handle 15 and the camera housing 73 are connected to each other by a rigid and straight shaft 13 with a substantially circular cylindrical circumferential surface. The viewing direction of a camera in the camera housing 73 is orthogonal to the longitudinal axis of the shaft 13.

In the transition area between the handle 15 and the shaft 13, a jacket 82 and guide blades 86 are arranged in a monolithic or substantially monolithic structural part. The jacket 82 surrounds a rotor for generating a substantially laminar air flow 58, guided and shaped by the jacket 82 and the guide blades 86, along the shaft 13 to the camera housing 73. As it continues on its way, the air flow 58 washes round the camera housing 73 and thus increases the heat removal from the surface of the latter.

Figure 10:
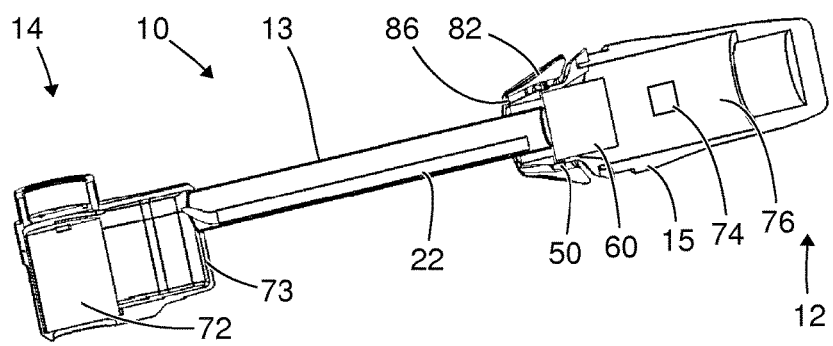
FIG. 10 shows a schematic axonometric cross-sectional view of the exoscope from FIG. 9.

FIG. 10 shows a further schematic axonometric view of the exoscope 10 from FIG. 9. The exoscope 10 in FIG. 10 is shown cut open along a plane that contains the axis of symmetry of the outer surface of the shaft 13 and the optical axis of a camera 72 in the camera housing 73. The cross section shown in FIG. 10 reveals the rotor 50 surrounded by the jacket 82, means 60 for generating a variable magnetic field for driving the rotor 50 in the transition area between handle 15 and shaft 13, and an installation space 76 in the handle 15 for a processor or other circuitry 74 for preparing or processing an image signal or for other heat sources. Moreover, the figure shows a bundle of optical fibers 22 provided in the shaft 13, for carrying illumination light from a light source in the installation space 76 in the handle 15 to the distal end 14 of the exoscope 10, and also a camera 72 in the camera housing 73.

Figure 11:
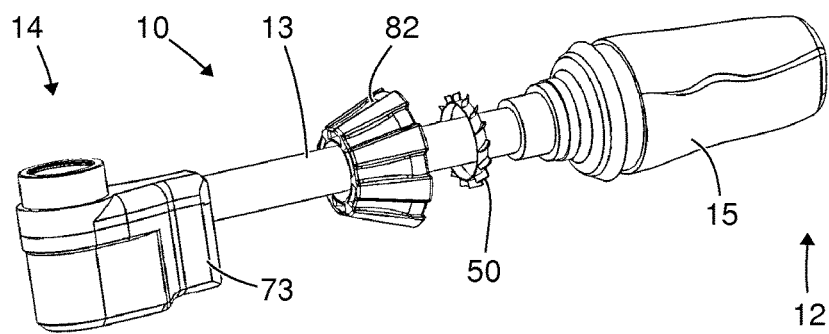
FIG. 11 shows a further schematic axonometric view of the exoscope from FIGS. 9 and 10.

FIG. 11 shows a further schematic axonometric view of the exoscope from FIGS. 9 and 10. The nature of the view in FIG. 11 is similar to that in FIG. 9. In contrast to FIGS. 9 and 10, the exoscope 10 in FIG. 11 is shown in a configuration which is suitable not for operating or using the exoscope 10 but instead for cleaning it. The jacket 82 with guide blades 86 and the rotor 50 have been moved in the distal direction starting from their positions intended for operation or use of the exoscope 10 in the transition area between handle 15 and shaft 13. In this way, the surfaces of the rotor 50, and surfaces in the area of the jacket and of the guide blades 86, are accessible for cleaning. The remaining outer surfaces of the exoscope 10 are in particular formed by several surface components that are joined to one another free of seams, in particular by cohesive bonding, in order to facilitate simple and complete cleaning.

The invention claimed is:

1. A medical instrument comprising:
 a liquid-tight sheath having an outer surface;
 a heat source disposed inside the liquid-tight sheath;
 a surface area of the outer surface being thermally coupled to the heat source;
 a rotor arranged around the outer surface of the sheath and configured to generate a flow of fluid at the surface area to remove thermal output generated by the heat source;
 a magnet disposed on the rotor; and
 a means for generating a variable magnetic field in order to move the rotor, the means being arranged inside the sheath.

2. The medical instrument as claimed in claim 1, wherein the means for generating a variable magnetic field generates a rotating magnetic field.

3. The medical instrument as claimed in claim 1, wherein the rotor includes a magnetic bearing that is supported free of contact by said means for generating a variable magnetic field.

4. The medical instrument as claimed in claim 3, wherein the rotor does not touch the sheath.

5. The medical instrument as claimed in claim 1, wherein the rotor has blades generating the flow of fluid in a direction from a proximal end to a distal end of the medical instrument when the rotor is rotating.

6. The medical instrument as claimed in claim 1, wherein the rotor has blades to generate the flow of fluid at a distal end of the medical instrument.

7. The medical instrument as claimed in claim 1, wherein the rotor is arranged at or near a distal end of the medical instrument.

8. The medical instrument as claimed in claim 1, wherein the rotor is movable in a direction parallel to a longitudinal axis of the medical instrument.

9. The medical instrument as claimed in claim 8, wherein at least one of:
 the means for generating a variable magnetic field is movable between several positions along a length of the medical instrument; or
 the medical instrument comprises several means for generating a variable magnetic field, each means for generating a variable magnetic field being disposed at one of several positions along the length of the medical instrument;
 such that the rotor is configured to be driven at each of the several positions.

10. The medical instrument as claimed in claim 1, wherein the rotor is configured to be magnetically decoupled and removed from being concentric with the sheath.

11. The medical instrument as claimed in claim 1, further comprising:
 a controller controlling at least one of a rotational direction or a rotational speed of the rotor by adjusting the variable magnetic field.

12. The medical instrument as claimed in claim 11, further comprising:
  means for detecting a temperature of the heat source;
  wherein the controller is coupled to the means for detecting the temperature and controls at least one of the rotational direction or the rotational speed of the rotor depending on the temperature of the heat source.

13. The medical instrument as claimed in claim 12, wherein said heat source is a first heat source, and said means for detecting a temperature of the heat source is a first means for detecting a temperature of the first heat source;
  the medical instrument further comprises a second heat source and a second means for detecting a temperature of the second heat source; and
  the controller is coupled to the second means for detecting the temperature of the second heat source and controls at least one of the rotational direction or the rotational speed of the rotor depending on the temperature of the first heat source and the temperature of the second heat source.

14. The medical instrument as claimed in claim 1, wherein the medical instrument is an endoscope with a long thin shaft or an exoscope or a surgical microscope.

15. The medical instrument as claimed in claim 1, further comprising:
  a guiding means for guiding or diverting the flow of fluid generated by the rotor.

16. The medical instrument as claimed in claim 15, wherein at least one of the rotor or the guiding means generates the flow of fluid to extend, at least in part, helically around a shaft of the medical instrument.

17. The medical instrument as claimed in claim 15, wherein the guiding means comprises a jacket configured to keep the flow of fluid at least at a portion of the surface area thermally coupled to the heat source.

18. The medical instrument as claimed in claim 15, wherein the guiding means comprises at least one a guide blade configured for at least one of:
  guiding the flow of fluid in a direction,
  shaping the flow of fluid to a cross section, or
  adjusting a speed profile of the flow of fluid.

19. The medical instrument as claimed in claim 1, wherein the flow of fluid comprises a laminar flow; and
  the medical instrument further comprises means for converting the laminar flow to a turbulent flow.

20. The medical instrument as claimed in claim 19, wherein the means for converting the laminar flow to a turbulent flow comprises a turbulator disposed on the outer surface of the sheath.

21. The medical instrument as claimed in claim 1, wherein the flow of fluid is a flow of ambient air and is produced for removal of thermal output generated by the heat source.

* * * * *